United States Patent
Stultz

(10) Patent No.: US 7,192,414 B2
(45) Date of Patent: Mar. 20, 2007

(54) PROGRAMMABLE IMPLANTABLE PUMP WITH ACCESSORY RESERVOIRS AND MULTIPLE INDEPENDENT LUMEN CATHETER

(75) Inventor: Mark R Stultz, Maple Grove, MN (US)

(73) Assignee: Advanced Bionics Corporation, Valencia, CA (US)

( * ) Notice: Subject to any disclaimer, the term of this patent is extended or adjusted under 35 U.S.C. 154(b) by 0 days.

(21) Appl. No.: 11/023,931

(22) Filed: Dec. 28, 2004

(65) Prior Publication Data

US 2005/0113745 A1  May 26, 2005

Related U.S. Application Data

(63) Continuation of application No. 10/099,060, filed on Mar. 15, 2002, now Pat. No. 7,083,593.

(60) Provisional application No. 60/284,771, filed on Apr. 18, 2001.

(51) Int. Cl.
*A61M 31/00* (2006.01)
(52) U.S. Cl. .................................. 604/93.01
(58) Field of Classification Search ............. 604/93.01, 604/94.01, 95.01, 65, 66, 67; 128/DIG. 12, 128/13
See application file for complete search history.

(56) References Cited

U.S. PATENT DOCUMENTS

| | | | |
|---|---|---|---|
| 4,003,379 A * | 1/1977 | Ellinwood, Jr. ........... | 604/891.1 |
| 4,072,146 A * | 2/1978 | Howes ........................ | 600/487 |
| 4,373,527 A | 2/1983 | Fischell | |
| 4,443,218 A | 4/1984 | DeCant, Jr. et al. | |
| 4,449,983 A | 5/1984 | Cortese et al. | |
| 4,588,394 A | 5/1986 | Schultz et al. | |
| 4,634,427 A | 1/1987 | Hannula et al. | |
| 4,871,351 A * | 10/1989 | Feingold ....................... | 604/66 |
| 4,894,057 A * | 1/1990 | Howes ....................... | 604/523 |
| 5,207,642 A * | 5/1993 | Orkin et al. .................. | 604/65 |
| 5,240,713 A | 8/1993 | Ayer | |
| 5,607,393 A | 3/1997 | Ensminger et al. | |
| 5,718,678 A * | 2/1998 | Fleming, III ................. | 604/43 |
| 6,436,091 B1 | 8/2002 | Harper et al. | |
| 6,471,688 B1 * | 10/2002 | Harper et al. ............. | 604/892.1 |
| 6,520,936 B1 * | 2/2003 | Mann ......................... | 604/141 |
| 6,554,822 B1 * | 4/2003 | Holschneider et al. ... | 604/892.1 |
| 6,902,544 B2 * | 6/2005 | Ludin et al. ............. | 604/93.01 |
| 2002/0188327 A1 | 12/2002 | Struble | |

FOREIGN PATENT DOCUMENTS

WO    WO-02/072178 A1    9/2002

* cited by examiner

*Primary Examiner*—Manuel Mendez
(74) *Attorney, Agent, or Firm*—Henricks, Slavin & Holmes LLP

(57) ABSTRACT

An implantable pump system includes: an implantable pump having separate chambers or reservoirs; and a catheter having two or more reservoir-specific inlet ports directed into respective lumens of the catheter. In one embodiment, the distal tips of the respective lumens may be directed to different sites within the patient's body, thereby allowing site specific and independent delivery of the medications stored in the respective pump chambers or reservoirs to be administered to different body sites at independently controlled times and rates. In another embodiment, the distal tips of the respective lumens are directed, more or less, to the same body site or tissue region, thereby providing for the independent delivery of multiple medications to the same regions at independently controlled times and rates.

16 Claims, 4 Drawing Sheets

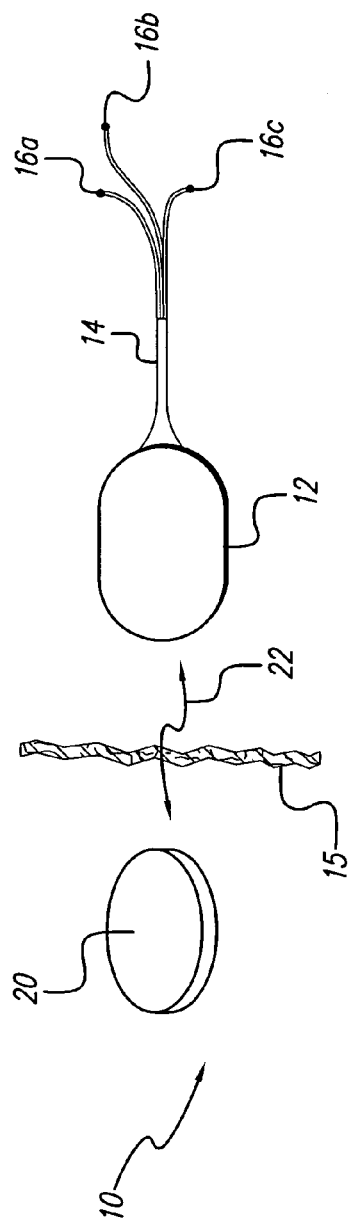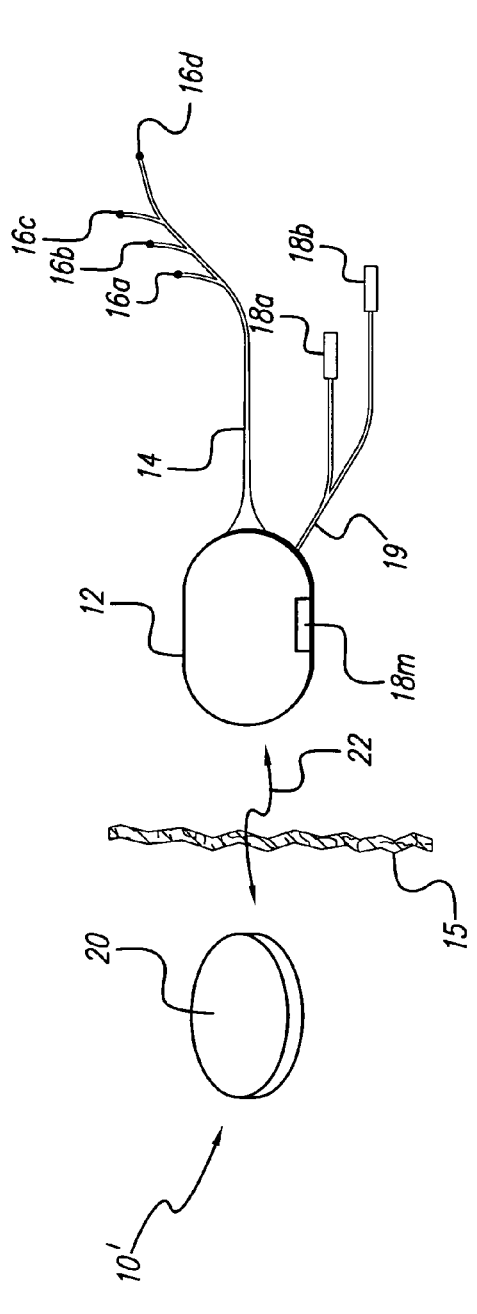

PROGRAMMABLE IMPLANTABLE PUMP WITH ACCESSORY RESERVOIRS AND MULTIPLE INDEPENDENT LUMEN CATHETER

The present application is a continuation of U.S. patent application Ser. No. 10/099,060, filed Mar. 15, 2002, now U.S. Pat. No. 7,083,593, which application claims the benefit of U.S. Provisional Application Ser. No. 60/284,771, filed Apr. 18, 2001. Both applications are herein incorporated by reference in their entireties.

BACKGROUND OF THE INVENTION

The present invention relates to implantable medical devices, and more particularly to an implantable programmable pump having multiple reservoirs and a multiple lumen catheter through which independent medications may be delivered to a patient at programmed times or upon demand.

Patients typically require short bursts of independent medications delivered at unique times. Such medications, or drugs, may be delivered via independently accessed reservoirs or may be bolused on demand via a suitable controller. Patients experiencing pain, and receiving medication therefor, may require a short acting, independently-delivered, analgesic rather than an incremental bolus of an admixture or of morphine alone. Spasticity patients may require a burst of pain medications in addition to anti-spasticity medications, or another drug to temporarily increase tone during patient transfers, or other critical times. For example, a cocktail mixture of pain medication in conjunction with another drug that counteracts baclofen for a short period of time may also assist in patient transfers, or other critical times when the patient's muscles require increased tone.

U.S. Pat. No. 4,588,394 teaches a totally subcutaneously implantable infusion reservoir and pump system that includes a variable capacity reservoir for receiving and storing fluids containing medications for delivery to a catheter, which catheter directs the medications to a specific infusion location in the body. A pump and valving arrangement is interposed between the reservoir and the catheter to facilitate and control the transfer of the medications from the reservoir to the catheter in a safe and efficient manner. There is no provision for the delivery of multiple medications through the same catheter.

U.S. Pat. No. 4,449,983 discloses an osmotic device that delivers two beneficial drugs to an environment of use. The device comprises a wall surrounding a lumen divided into a first compartment containing a drug that is separated by a hydrogel partition from a second compartment containing a different drug. An orifice through the wall communicates with the first compartment for delivering drug formulation from the first compartment, and another orifice through the wall communicates with the second compartment for delivering drug formulation from the second compartment. In use, drug formulation is dispensed separately from each compartment by fluid being imbibed through the wall of the device into each compartment at a rate controlled by the permeability of the wall and the osmotic pressure gradient across the wall against the drug formulation in each compartment. A solution is thus produced in each compartment containing drugs. Through the expansion and swelling of the hydrogel, the drug formulation is dispensed through the respective orifices at a controlled and continuous rate over a prolonged period to time. There is no provision for bolus drug delivery over a short period of time, or for programmed rates of delivery.

U.S. Pat. No. 5,240,713 teaches a dual rate agent delivery device that provides for the controlled delivery of a beneficial agent in a hydrophilic carrier, followed by a continuous and sustained delivery of an agent in a controlled and uniform amount over a prolonged period of time. However, the dual rates are not programmable, but are rather controlled through the physical attributes of the device and osmotic pumping. The U.S. Pat. No. 5,240,713 further provides a comprehensive list of prior art relating to drug delivery devices.

What is needed is an implantable pump capable of independently delivering multiple medications at independently programmable rates.

SUMMARY OF THE INVENTION

The present invention addresses the above and other needs by providing an implantable pump system that includes: (1) an implantable pump having separate chambers or reservoirs, at least one of which is coupled to the pump so as to allow a programmable rate of delivery of the medication stored in the pump chamber or reservoir, the other chambers or reservoirs of which are at least capable of delivery a bolus via a pressurized, and potentially independently programmable chamber or pumping mechanism; (2) a patient controller that enables the actuation of the pump so as to administer a bolus or programmed rate of the first, second, third, . . . or nth medication contained in the independent chambers or reservoirs coupled to the pump; and (3) a catheter having two or more reservoir-specific inlet ports directed into respective lumens of the catheter.

In one embodiment, the distal tips of the respective lumens may be directed to different sites within the patient's body, thereby allowing site specific and independent delivery of the medications stored in the respective pump chambers or reservoirs to be administered to different body sites at independently controlled times and rates.

In another embodiment, the distal tips of the respective lumens are directed, more or less, to the same body site or tissue region, thereby providing for the independent delivery of multiple medications to the same regions at independently controlled times and rates.

Advantageously the medications administered through use of the implantable pump having multiple chambers and delivery lumens may comprise drugs, biologics, proteins, genetic materials, and any other substance or material which medical personnel may prescribe as being beneficial for the patient to receive.

An important feature of the present invention is the programmability of the pump, which allows different medications to be delivered through independent lumens at different times and rates. In one embodiment, such programming may be done electronically, based on a clock or different times of the day. In another embodiment, one or more body sensors are coupled with the pump and are adapted to sense various physiological parameters, such as muscle tone, heart rate, respiration rate, blood oxygen saturation, physical activity, temperature, glucose level, and the like. In accordance with the use of such sensor(s), when certain physiological conditions are sensed by the sensor(s), the pump is actuated so as to deliver a programmed amount of one or more medications selected as a function of the sensed physiological condition. For example, if a sudden, fast heart rate is sensed, an appropriate medication may be administered in an attempt to slow the heart rate.

It is thus a feature of the present invention to provide an a multi-chamber programmable, implantable pump.

It is a further feature of the invention to provide a multi-lumen catheter for use with such pump through which multiple medications may be independently delivered by the pump.

BRIEF DESCRIPTION OF THE DRAWINGS

The above and other aspects, features and advantages of the present invention will be more apparent from the following more particular description thereof, presented in conjunction with the following drawings wherein:

FIG. 1 shows an implantable pump system made in accordance with one embodiment of the invention;

FIG. 2 shows an implantable pump system made in accordance with another embodiment of the invention;

Corresponding reference characters indicate corresponding components throughout the several views of the drawings.

DETAILED DESCRIPTION OF THE INVENTION

Figure 3:
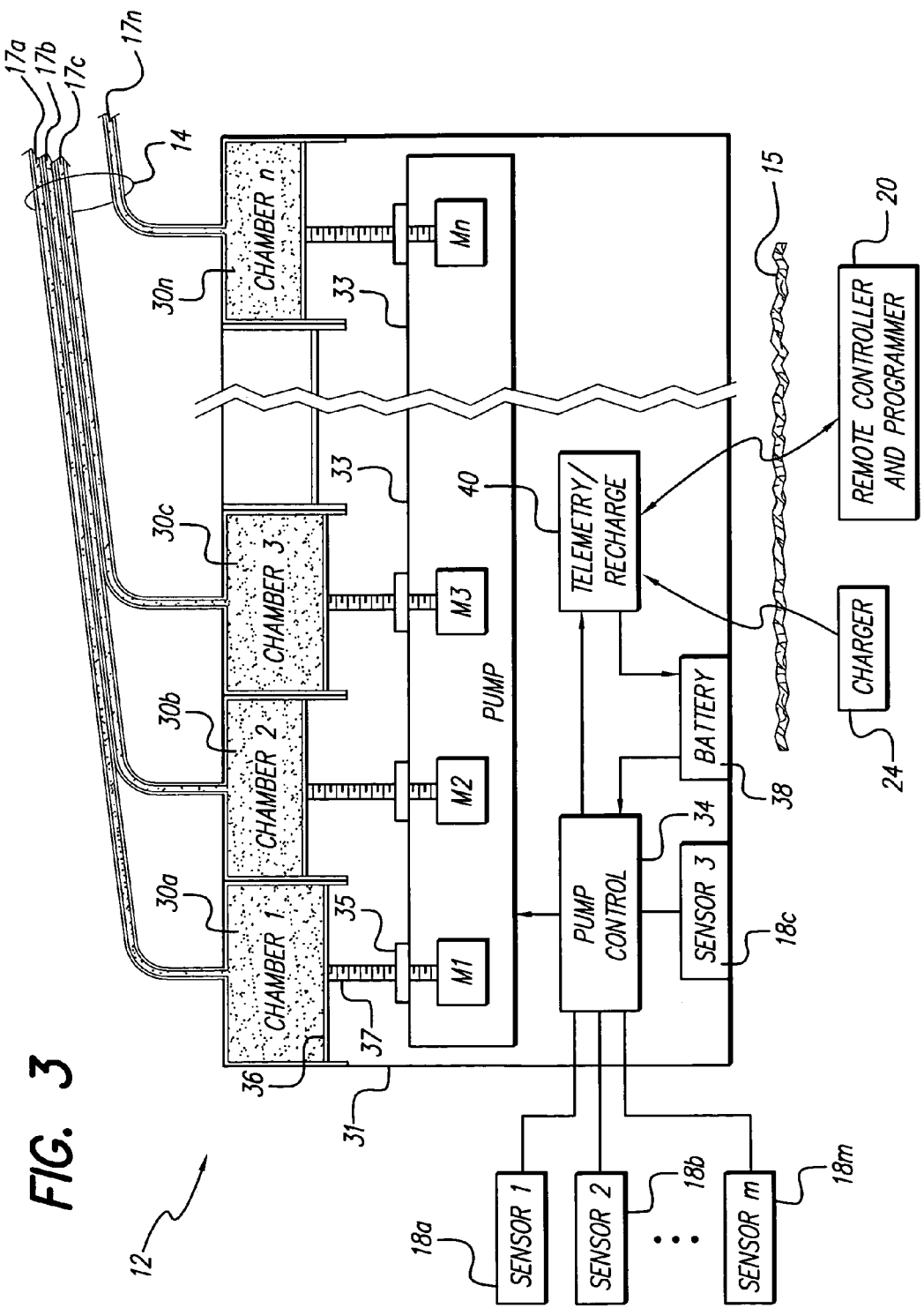
FIG. 3 is a functional block diagram of the pump system of the present invention.

The following description is of the best mode presently contemplated for carrying out the invention. This description is not to be taken in a limiting sense, but is made merely for the purpose of describing the general principles of the invention. The scope of the invention should be determined with reference to the claims.

Turning first to FIG. 1, a pump system 10 made in accordance with one embodiment of the invention is illustrated. The system 10 includes an implantable pump 12 coupled to a multi-lumen catheter 14. The pump 12, which includes multiple chambers or reservoirs, control electronics and a pumping mechanism, all housed within a suitable case, as described in more detail below in conjunction with FIG. 3, along with the multi-lumen catheter 12, are adapted to be implanted beneath the skin 15 of the patient. Typically, the location where the pump is implanted is in the chest or abdomen area of the patient, but may be implanted in any location in the patient's body.

The multi-lumen catheter 14 includes a multiplicity of independent lumens therein, each terminating at a distal tip 16. For the embodiment shown in FIG. 1, three lumens are employed within the catheter 14, each having a distal tip 16a, 16b and 16c that terminate near the same tissue location. Hence, the embodiment shown in FIG. 1 is particularly adapted for use when one or more medications, e.g., three medications, need to be independently delivered to approximately the same tissue location. The use of three lumens within the multi-lumen catheter 14 is only exemplary, as any number of lumens, e.g., from two to ten lumens, may be employed as circumstances warrant.

Advantageously, each medication delivered through the multi-lumen catheter 14 may be delivered at its own programmed rate and/or start/stop time. The medications administered through the delivery lumens 16a, 16b, 16c, . . . may comprise drugs, biologics, proteins, genetic materials, and any other substance or material which medical personnel may prescribe as being beneficial for the patient to receive.

Programming or control of the implantable pump 12 shown in FIG. 1 is accomplished through the use of an external (non-implanted) control unit 20. The control unit 20 communicates with the implantable pump 12 via a telecommunications link 22, which link 22 is represented in FIG. 1 by a wavy arrow. Such link 22 may be of any type known in the art, e.g., a radio frequency (rf) link, an acoustic link, an IR or other optical link, an inductive link, a magnetic link, or the like. Using such link, command words (or other command signals) are sent from the remote control unit 20 to the implantable pump 20 where they are received and acted upon. Such control or command words may control the pump, e.g., turn the pump ON or OFF, or set, i.e., program, various pump parameters used within the pump, e.g., the rate of delivery of a given medication, the time at which delivery of a medication is to commence, the time at which delivery of a medication is to end, and the like.

Additionally, at least in some embodiments of the invention, the implantable pump 12 sends status signals, e.g., back-telemetry signals, to the remote control unit 20 through the telecommunications link 22. Such status signals provide information to the remote user, by way of a display included on, or coupled to, the remote unit 20 relative to the performance and status of the pump 20. Such back-telemetry data indicates, e.g., the state of charge of a battery included as part of the pump, the amount of medication remaining in its multiple reservoirs or chambers, the amount of medication that has been delivered through a given lumen of the catheter during a specified time period, and the like. Back telemetry may also be used, when sensors 18 are employed with the device, e.g., as shown in FIG. 2 described below, to report sensed physiological parameters or other sensor metrics of physiologic conditions, all of which data is telemetered to a remote programmer 20 or other remote device for analysis and/or display. The remote device may also stored such data for subsequent display and/or analysis.

Next, as seen in FIG. 2, a pump system 10' made in accordance with another embodiment of the invention is shown. Like the system 10 shown in FIG. 1, the system 10' of FIG. 2 includes a programmable implantable pump 12 connected to a multi-lumen catheter 14. A remote control unit 20 in telecommunicative contact with the pump 12 via a suitable telecommunications link 22 also is included as part of the system 10'. The remote control unit 20 is used to control and/or program the implantable pump 12, as well as to monitor the performance status of the implantable pump 12, or sensed physiological conditions, as previously described. Unlike the system 10 of FIG. 1, the distal tips 16a, 16b, 16c, 16d of the multiplicity of lumens included within the multi-lumen catheter system 10' of FIG. 2 are adapted to terminate at different distal locations, thereby facilitating the delivery of specific medications to different tissue locations.

Additionally, unlike the system 10 of FIG. 1, the system 10' of FIG. 2 includes a plurality of sensors 18 that are connected to, or included as an integral part of, the pump 12. For example, first and second sensors 18a and 18b are coupled to the pump 12 via a suitable connection cable 19, while a third sensor 18m is mounted within or on the housing of the pump 12. Such sensors 18a, 18b and 18c are adapted to sense a physiological condition of the patient's body within which the pump unit 12 is implanted, and to respond to such sensed physiological condition in accordance with a preprogrammed protocol. For example, sensor 18a may sense the body temperature of the patient, and in response to sensing a high temperature, i.e., a temperature above a preset threshold, the pump 12 may be preprogrammed to deliver a prescribed quantity of a specific medication to the patient aimed to reduce the temperature below the preset threshold. The sensor 18b, in a similar manner, may sense the glucose level present in body fluids, and in response to sensing a glucose level that is out of range of predetermined acceptable levels, cause the pump 12 to take appropriate corrective action by delivering an appropriate medication(s) through one or more the lumens of the multi-lumen catheter 14. The sensor 18m, similarly, may sense the physical activity of the patient's body, and in response to sensing physical activity (i.e., sensing that the patient is active), cause the pump to deliver a first medication, or a first combination of medications, through at least one of the lumens of the multi-lumen catheter 14; and in response to not sensing physical activity (i.e., sensing physical inactivity), cause the pump to deliver a second medication, or a second combination of medications, through at least one of the lumens of the multi-lumen catheter.

The types of physiological parameters that may be sensed by the sensors 18a, 18b, . . . 18m include, but are not necessarily limited to, muscle tone, heart rate, respiration rate, blood oxygen saturation, tissue impedance, physical activity, body position (e.g., lying, sitting or standing), body temperature, glucose level, and the like. As has been indicated, signals representative of the physiological parameters sensed by the sensors 18a, 18b, 18c, . . . 18m may be telemetered to an external device, e.g., to the remote programmer 20, for storage, display, or analysis.

Turning next to FIG. 3, a functional block diagram of a representative programmable, implantable pump made in accordance with the present invention is illustrated. It is to be emphasized that that which is shown in FIG. 3 is functional, and not necessarily representative of the actual hardware components that may be used by the implantable pump 12. Those of skill in the art, given the functional description presented herein, may fashion numerous types of hardware components in order to achieve the functions represented.

As seen in FIG. 3, the pump 12 includes a multiplicity of chambers, or reservoirs 30a, 30b, 30c, . . . 30n, wherein desired medications may be stored. Each chamber 30a, 30b, 30c, . . . 30n has a corresponding lumen 17a, 17b, . . . 17n in fluid communication therewith. Each lumen terminates at a distal port 16a, 16b, . . . 16n (not shown in FIG. 3, but seen in FIGS. 1 and 2) whereat the medication held in the respective chamber 30a, 30b, . . . may be dispensed.

Each chamber 30a, 30b, . . . 30n has a pump mechanism associated therewith that causes the medication stored in the respective chamber to be dispensed through the respective lumen at a programmed rate and/or at a programmed delivery time. By way of functional illustration only, the pump mechanism associated with chambers 30a includes a miniature stepping motor M1 that drives a lead screw 37 passing through an anchored lead nut 35. A distal end of the lead screw 37 attaches to movable diaphragm 36, which diaphragm forms one wall of the chamber 30a. As the lead screw 37 rotates a fixed rotational amount, under control of the stepper motor M1, the distal end of the lead screw, and hence the diaphragm 36, advances a fixed amount, causing a fixed volume of medication within chamber 30a to be dispensed through lumen 17a.

In a similar manner, additional miniature stepper motors M2, M3, . . . Mn, control respective lead screws coupled to movable diaphragms of chambers 30b, 30c, . . . 30n, thereby allowing controlled volumes of medication stored in chambers 30b, 30c, . . . 30n to be dispensed through lumens 17b, 17c, . . . 17n, respectively.

The chambers 30a, 30b, 30c, . . . 30n may be realized using a balloon made from a suitable stretchable material, e.g., silicone rubber or Silastic, and the movable diaphragm 36 may be a wall or plunger that collapses against one side of the balloon, forcing the liquid contents of the balloon, i.e., the medication stored therein, to be dispensed through the respective lumen.

The stepper motors M1, M2, M3, . . . Mn are controlled by respective driver circuits contained within the pump control circuitry 34. Such control circuitry includes, in addition to the pump driver circuits, suitable logic circuitry for controlling operation of the pumps in accordance with programmed parameters. The logic circuitry may comprise a state machine and/or a microprocessor. The programmed parameters are stored in suitable memory circuitry, as is known in the art. The parameters that may be stored in the memory circuitry include, for each stepper motor or equivalent pump activation mechanism, dispense start time, dispense stop time, max dispensed volume, and rate.

Operating power for the pump control circuitry 34 and the stepper motors M1, M2, M3 . . . Mn is provided by a suitable battery 38. The battery 38 may be a primary Lithium Ion battery that has sufficient energy stored therein to power the operation of the pump control circuitry 34 for 3–10 years, or a rechargeable battery, e.g., a rechargeable Lithium Ion battery, as is known in the art.

A telemetry/recharge circuit 40 allows programming signals and recharge energy to be received from an external remote control/programmer unit 20 or an external charger unit 24. In one embodiment, the telemetry/recharge circuit 40 includes a coil that is inductively linked with another coil included within the remote control/programmer unit 20 or the remote charger 24. A carrier signal is coupled from the remote coil to the implanted coil. Energy contained within the carrier signal is used to recharge the battery 38. Control and/or programming data is transferred to the implantable unit 12 by modulating the carrier signal. Back-telemetry may occur in the same manner, but at a different frequency. Other forms of data/energy transfer may also be employed, as needed or as appropriate.

One or more physiological sensors 18a, 18b, 18c, . . . 18m may optionally be used with the implantable pump in order to provide physiological feedback to the pump control circuits in order to control the medication delivery in an appropriate manner. The use of such physiological sensors was described previously in connection with the description of FIG. 2.

All of the components of the pump 12, except one or more of the optional sensors 18a, 18b, . . . 18m, are housed in an implantable housing 31. The miniature stepper motors M1, M2 . . . Mn may be housed within a separate enclosure 33 included within the housing 31. The housing 31 is preferably of a size and shape that facilitates its implantation under the skin 15 of a patient. Typically, such shape will comprise a relatively flat case, having rounded corners, much like existing implantable pacemakers or cochlear stimulators.

Figure 3A:
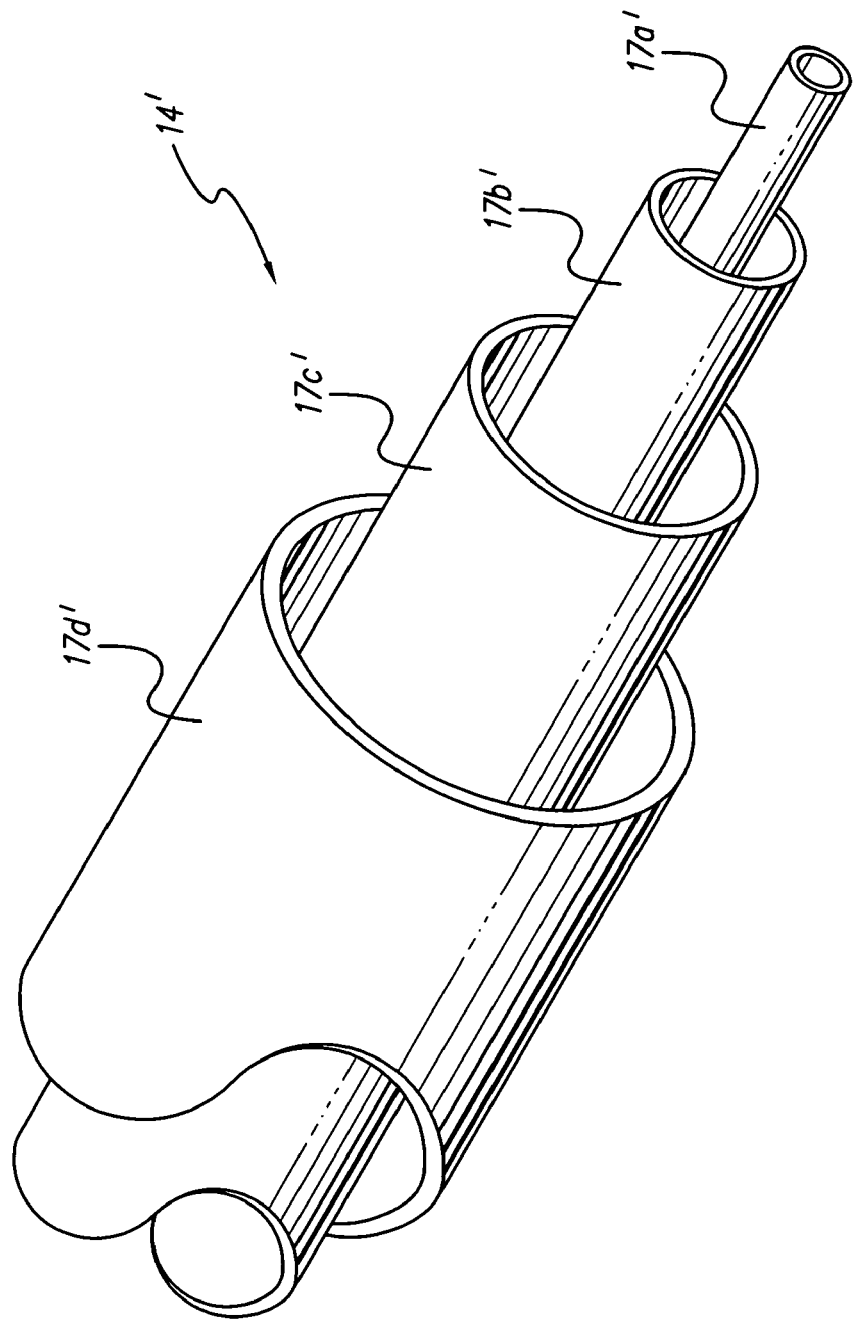
FIG. 3A depicts an alternate embodiment of a multi-lumen catheter that may be used with the invention.

An alternative embodiment of a multi-lumen catheter 14' that may be used with the invention is illustrated in FIG. 3A. Such alternative embodiment includes multiple coaxial lumens 17a', 17b', 17c' and 17d'. As seen in FIG. 3A, the lumen 17a' has the smallest diameter, and fits within the lumen 17b'. The lumen 17b' similarly fits within the lumen 17c', and the lumen 17c' fits within the lumen 17d'. Such alternative embodiment of a coaxial multi-lumen catheter 14' may have different volumes associated with each lumen, thereby facilitating the dispensing of different volumes of fluid or other medications at the same time. That is, the actual volume remaining within each lumen 17a', 17b', 17c' or 17d' for delivery of a medication, after subtracting out the volume occupied by the other coaxial lumens, may differ significantly. In contrast, a multi-lumen catheter 14 (seen best in FIG. 4) shows multi-lumens of more or less the same diameter, all contained within the same sheath. Of course, multi-lumens contained within the same sheath could also have different diameters, as needed or desired for a given application.

Figure 4:
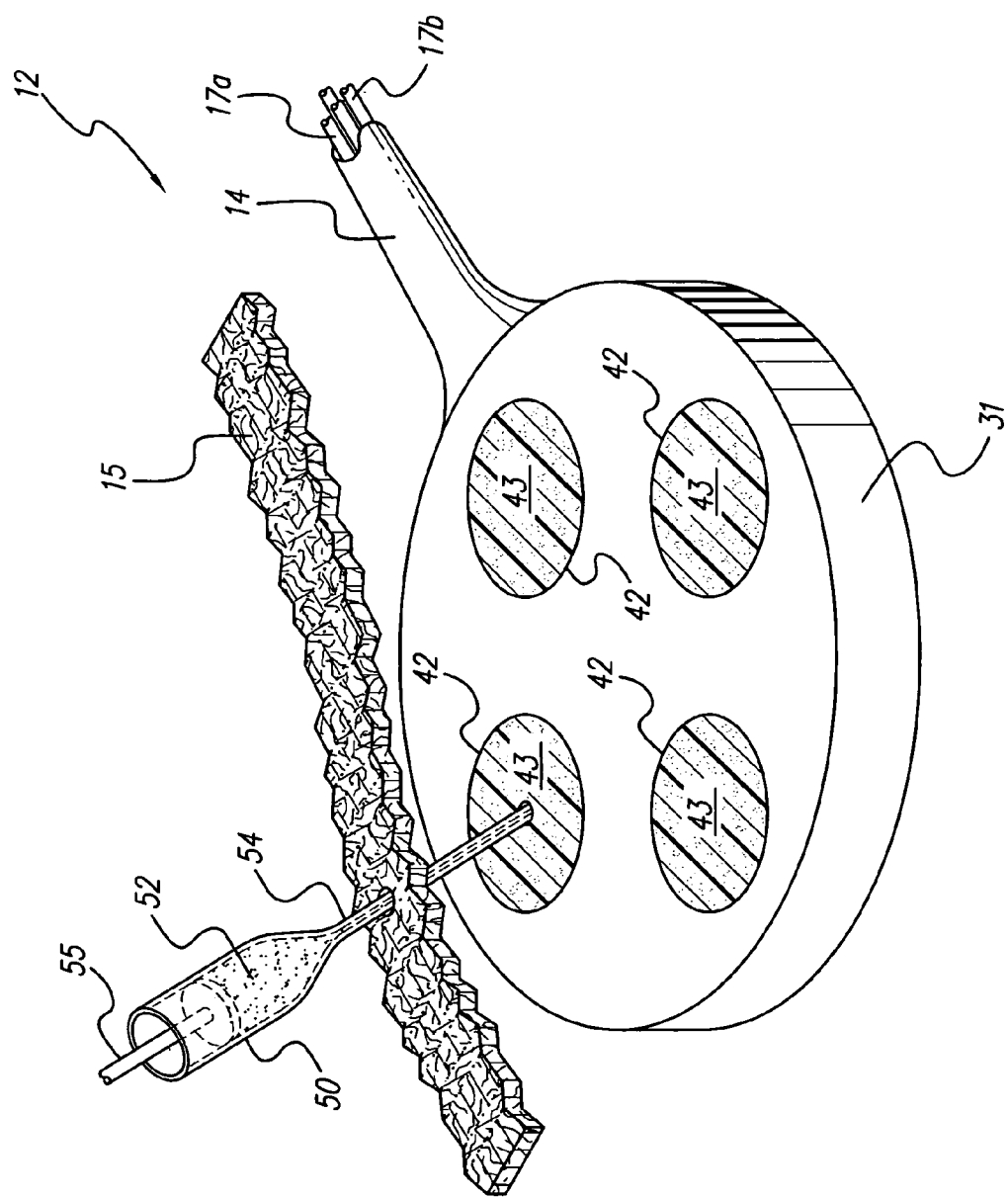
FIG. 4 depicts one method that may be used to refill the independent reservoirs or storage chambers used with the pump system of the present invention.

Next, with reference to FIG. 4, one technique for refilling the chambers 30a, 30b, 30c, . . . 30n with a suitable medication is illustrated. For the embodiment contemplated, the case or housing 31 of the implantable pump 12 includes a plurality of windows 42 closed with a suitable septum material 43. The septum material 43 forms one wall or side of the respective chambers 30a, 30b, . . . 30n included within the housing 31. The windows 42 are positioned so as to lie just under the skin 15 of the patient within whom the pump 12 is implanted. A doctor, or other medical personnel, fills a syringe 50 with medication 52 that is to be placed within one of the chambers 30a, 30b, . . . or 30n of the pump. The location of the desired window 42 under the skin 15 is ascertained, e.g., by pushing with a finger or other device. Then, a needle 54 of the syringe 50 is pushed through the skin 15 and through the septum 43 of the desired window 42, and a specified amount of the medication 52 is injected into the chamber 30a, 30b, . . . or 30n by pushing on a plunger 55 of the syringe 50.

As described above, it is thus seen that the present invention provides a multi-chamber programmable, implantable pump having a multi-lumen catheter through which multiple medications may be independently delivered to the same or different tissue locations by the pump.

While the invention herein disclosed has been described by means of specific embodiments and applications thereof, numerous modifications and variations could be made thereto by those skilled in the art without departing from the scope of the invention set forth in the claims.

What is claimed is:

1. An implantable medication delivery apparatus for use with an external controller, the apparatus comprising:
    a single implantable housing;
    a plurality of medication-storage chambers within the single implantable housing;
    a pump apparatus within the single implantable housing and operably connected to the plurality of medication-storage chambers;
    a plurality of lumens in fluid communication with a respective one of the plurality of medication-storage chambers; and
    a controller, within the single implantable housing and operably connected to the pump apparatus, configured to control the pump apparatus to pump medication from one of the medication-storage chambers at a predetermined basal rate and to control the pump apparatus to pump a bolus of medication from another one of the medication-storage chambers in response to a bolus delivery signal from the external controller.

2. An implantable medication delivery apparatus as claimed in claim 1, wherein the plurality of medication-storage chambers comprises at least three medication-storage chambers.

3. An implantable medication delivery apparatus as claimed in claim 1, wherein the plurality of medication-storage chambers are located between the pump apparatus and the plurality of lumens.

4. An implantable medication delivery apparatus as claimed in claim 1, wherein the plurality of lumens are located within a single catheter.

5. An implantable medication delivery apparatus as claimed in claim 1, wherein the pump apparatus comprises a plurality of individual pumps.

6. An implantable medication delivery apparatus as claimed in claim 5, wherein each of the individual pumps includes a movable diaphragm.

7. An implantable medication delivery apparatus as claimed in claim 6, wherein each of the individual pumps includes a motor connected to the movable diaphragm.

8. An implantable medication delivery apparatus as claimed in claim 1, the apparatus further comprising:
    a physiological sensor operably connected to the controller.

9. An implantable medication delivery apparatus for use with an external controller, the apparatus comprising:
    a single implantable housing;
    a plurality of medication-storage chambers within the single implantable housing;
    a pump apparatus within the single implantable housing and operably connected to the plurality of medication-storage chambers;
    a plurality of lumens in fluid communication with a respective one of the plurality of medication-storage chambers; and
    means, within the single implantable housing and operably connected to the pump apparatus, for controlling the pump apparatus to pump medication from one of the medication-storage chambers at a predetermined basal rate and controlling the pump apparatus to pump a bolus of medication from another one of the medication-storage chambers in response to a bolus delivery signal from the external controller.

10. An implantable medication delivery apparatus as claimed in claim 9, wherein the plurality of medication-storage chambers comprises at least three medication-storage chambers.

11. An implantable medication delivery apparatus as claimed in claim 9, wherein the plurality of medication-storage chambers are located between the pump apparatus and the plurality of lumens.

12. An implantable medication delivery apparatus as claimed in claim 9, wherein the plurality of lumens are located within a single catheter.

13. An implantable medication delivery apparatus as claimed in claim 9, wherein the pump apparatus comprises a plurality of individual pumps.

14. An implantable medication delivery apparatus as claimed in claim 13, wherein each of the individual pumps includes a movable diaphragm.

15. An implantable medication delivery apparatus as claimed in claim 14, wherein each of the individual pumps includes a motor connected to the movable diaphragm.

16. An implantable medication delivery apparatus as claimed in claim 9, the apparatus further comprising:
    a physiological sensor operably connected to the means for controlling the pump apparatus.

* * * * *